(12) United States Patent (10) Patent No.: US 8,231,550 B2
Teirstein et al. (45) Date of Patent: Jul. 31, 2012

(54) GUIDE WIRE LOADING METHOD AND APPARATUS WITH TOWEL ATTACHMENT MECHANISM

(75) Inventors: Paul S. Teirstein, La Jolla, CA (US); Osama Amine, Newark, NJ (US); William Atkinson, Escondido, CA (US); William Gould, Fallbrook, CA (US); Yem Chin, Burlington, MA (US); Paul Scopton, Winchester, MA (US); Robert F. Carmichael, Jr., Needham, MA (US)

(73) Assignee: Paul S. Teirstein, La Jolla, CA (US)

( * ) Notice: Subject to any disclaimer, the term of this patent is extended or adjusted under 35 U.S.C. 154(b) by 327 days.

(21) Appl. No.: 12/498,965

(22) Filed: Jul. 7, 2009

(65) Prior Publication Data

US 2010/0010377 A1 Jan. 14, 2010

Related U.S. Application Data

(63) Continuation-in-part of application No. 12/218,031, filed on Jul. 9, 2008.

(51) Int. Cl.
*A61B 5/00* (2006.01)
*A61B 19/00* (2006.01)
*A61B 19/08* (2006.01)
*A61F 5/37* (2006.01)
*A61F 11/00* (2006.01)
*A61M 25/00* (2006.01)

(52) U.S. Cl. ........ 600/585; 128/849; 128/852; 604/523; 604/528; 606/108

(58) Field of Classification Search .................. 600/585; 128/849–856; 206/338, 339, 363, 364, 365, 206/366, 370; 606/108
See application file for complete search history.

(56) References Cited

U.S. PATENT DOCUMENTS

| 4,185,636 | A | | 1/1980 | Gabbay et al. |
|---|---|---|---|---|
| 4,336,806 | A | | 6/1982 | Eldridge, Jr. |
| 4,492,229 | A | | 1/1985 | Grunwald |
| 4,820,274 | A | | 4/1989 | Choksi et al. |
| 4,835,824 | A | * | 6/1989 | Durham et al. ................. 24/339 |
| 4,907,332 | A | | 3/1990 | Christian et al. |
| 5,735,821 | A | * | 4/1998 | Dobkin ........................ 604/174 |
| 5,830,157 | A | | 11/1998 | Foote |
| 6,554,808 | B1 | | 4/2003 | Cook |
| 6,872,192 | B2 | | 3/2005 | Nash et al. |
| 7,303,568 | B2 | | 12/2007 | Jannot |
| 2002/0177789 | A1 | | 11/2002 | Ferry et al. |
| 2005/0182368 | A1 | | 8/2005 | Gillis et al. |
| 2006/0094987 | A1 | * | 5/2006 | van Erp et al. ................ 600/585 |
| 2006/0149292 | A1 | | 7/2006 | Knudtson et al. |
| 2006/0253048 | A1 | | 11/2006 | Jones et al. |
| 2007/0118079 | A1 | | 5/2007 | Moberg et al. |

* cited by examiner

*Primary Examiner* — Max Hindenburg
*Assistant Examiner* — Devin Henson
(74) *Attorney, Agent, or Firm* — Mark D. Wieczorek, Esq.; Mayer & Williams PC (57) ABSTRACT

A device for loading a guide wire into the open end of a tubular instrument, such as a catheter. The device can be a block of material having a groove in its surface. The ends of the guide wire and the tubular instrument are placed into the groove and moved toward each other. When the ends meet, the groove guides the guide wire into the open end of the tubular instrument. The groove, or at least a portion of the groove, can have a cross-sectional contour that closely matches the outside radius of the tubular instrument. The groove can have a substantially vertical wall and a substantially non-vertical wall. A variety of attachment mechanisms may be provided for attaching the device to a towel draping a patient.

9 Claims, 12 Drawing Sheets

GUIDE WIRE LOADING METHOD AND APPARATUS WITH TOWEL ATTACHMENT MECHANISM

CROSS REFERENCE TO RELATED APPLICATIONS

This application is a continuation-in-part of U.S. patent application Ser. No. 12/218,031, filed Jul. 9, 2008, entitled "Guide Wire Loading Method and Apparatus", the entirety of which is incorporated by reference herein.

STATEMENT REGARDING FEDERALLY SPONSORED RESEARCH OR DEVELOPMENT

Not Applicable

BACKGROUND OF THE INVENTION

1. Field of the Invention

This invention is in the field of equipment used for intravascular medical procedures, such as guide wires, stents, angioplasty balloons, drilling burrs, and the catheters that are used to convey some of these.

2. Background Art

In the field of interventional cardiology, catheters and other tubular instruments are often run into a blood vessel by being threaded over a guide wire that has been placed into the blood vessel. So, it is often necessary to thread a very small diameter guide wire into the open end of a very small tubular instrument. The guide wires are usually about 0.014 inches in diameter, and the tubular instruments into which they are threaded can have diameters ranging from about 2 to 4 French. Catheters are often used to convey and operate various other types of instruments, such as balloons, stents, burrs, or radioactive segments. Many of these are also tubular in shape, and guide wires are often threaded through them. Because of the small diameters of the catheters, these other instruments, and the guide wires, it is very difficult to see and manipulate these members well enough to thread the guide wire into the tubular instrument very quickly. The speed and efficiency of every movement are important in interventional cardiology and other disciplines, as the blood flow in the blood vessel being used is often compromised.

It is the object of the present invention to provide a device, and a method for its use, which will quickly and efficiently thread a very small diameter guide wire into a very small diameter tubular instrument, such as a catheter. It is also an object of the present invention to provide a device for threading a guide wire into a tubular instrument that can be conveniently secured in place to an operating field.

BRIEF SUMMARY OF THE INVENTION

The present invention is a device for loading a guide wire into the open end of a tubular instrument such as a catheter. The device can be a block of material which has an open groove in its surface. The end of the guide wire and the open end of the tubular instrument are placed into the groove, and the two ends are moved toward each other. The guide wire and the tubular instrument can be angled above the device, with just their ends touching the groove and moving along the groove. When the ends meet, the groove guides the guide wire into the open end of the tubular instrument.

The groove, or at least a portion of the groove, can have a cross-sectional contour that closely matches the outside radius of the tubular instrument. The bottom of the groove is basically a concave surface. The bottom of the groove can have a radiused or rounded cross-sectional contour, or it can be formed by a plurality of substantially flat longitudinal surfaces intersecting at shallow angles (e.g., between about 125 degrees and 175 degrees), thereby approximating a rounded contour. In this case, the spaces created by the joints between the flat surfaces, between the groove surface and the catheter, must be small enough to prevent entry of the end of the guide wire between the catheter and the groove surface. In another implementation, the angles of the groove walls are not symmetric; while one may be vertical to arrest the guide wire and/or tubular instrument against lateral movement, the other may be angled to allow the guide wire and/or tubular instrument to be inserted more easily into the device. In any case, the radius and depth of the rounded or multi-surfaced contour can be sized to work best with any selected diameter of tubular instrument.

The groove can have a uniform depth and cross-sectional radius along its entire length. The groove also can be split into two end-to-end segments, with one segment or portion having a shallower depth, and/or a smaller radius, than the other segment or portion, thereby forming a discontinuity in the depth, and/or the radius, of the groove where the two portions meet. In this case, the guide wire is run in the shallower, and/or smaller radiused, portion of the groove, and the tubular instrument is run in the deeper, and/or larger radiused, portion. Preferably, the tubular instrument would first be run along the deeper, and/or larger radiused, portion of the groove until it butts up against the discontinuity in depth, and/or radius, where the two portions of the groove meet. Then, the guide wire would be run along the shallower, and/or smaller radiused, portion of the groove until its end enters the open end of the tubular instrument.

The device also can have a plurality of grooves on its surface, with each groove having a different depth, and/or cross-sectional radius, to make it substantially match the radius of a different diameter tubular instrument. Each groove can be labeled as to the size of tubular instrument with which it can best be used. Grooves having two different depths, and/or cross-sectional radii, can be so labeled.

The inner surface of the groove can have a slick surface, either because of the material from which the device is formed, the smoothness of the surface, or because of lubrication on the surface.

The device may have one or more attachment mechanisms to allow the same to be secured in an operating field onto, e.g., a fabric such as a towel draping a patient. The attachment mechanisms may be of a number of types of construction, and may include towel clamps with springs or clips, flexible fork assemblies, flexible tabs, hinged tabs, wire capture systems, gripping ring with flexible fingers, wire-and-plug capture systems, and opposing finger towel capture systems.

The novel features of this invention, as well as the invention itself, will be best understood from the attached drawings, taken along with the following description, in which similar reference characters refer to similar parts, and in which:

DETAILED DESCRIPTION OF THE INVENTION

Figure 1:
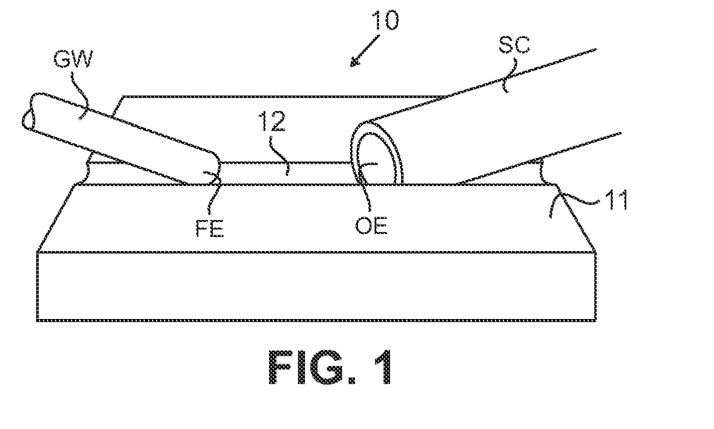
FIG. 1 is a perspective view of a device according to the present invention, in use with a guide wire and a catheter.

As shown in FIG. 1, a device 10 according to the present invention comprises a body 11, also termed a housing, made of any appropriate material, such as a plastic or metal. Formed within at least one surface of this body 11 is at least one open groove 12. Generally the groove is formed on a top surface of the body or housing. Various possible characteristics of the groove 12 are discussed below. In use, a guide wire GW has been introduced into a blood vessel of a patient (not shown). The free end FE of the guide wire GW is placed in the groove 12. The guide wire is held so that it is angled relative to the surface of the body 11, for example, at a 45 degree angle, as its free end FE is placed and held in the groove 12. A selected catheter SC is also held so that it is angled at a similar angle relative to the surface of the body 11, oriented toward the groove 12, and an open end OE of the catheter SC is placed in the groove 12. Rather than a catheter, any other type of tubular instrument may also be used with the present invention. The catheter, or any other tubular instrument for that matter, is referred to herein as a "selected" catheter, because it is selected for use in the medical procedure, at least partially because of its outside diameter. The groove 12 is designed to have dimensions that will function best with this selected outside diameter of the selected catheter SC. Once the respective ends FE, OE of the guide wire GW and the selected catheter SC are placed within the groove 12, the guide wire GW and the catheter SC are moved toward each other. Alternatively, one member may be held stationary, and the other member may be moved toward it. What matters is that the ends FE, OE of the two members are brought together in the groove 12. When the two ends FE, OE meet, the free end FE of the guide wire GW will enter the open end OE of the catheter SC, with both being guided by the groove 12.

It is usually helpful if the surface of the groove 12 is made "slick", either by being made very smooth, or by being lubricated, or both. In order to achieve lubrication, the body 11 of the device 10 may be formed of a lubricious material, such as various types of plastic, or lubrication can be provided by application of a lubricant in the groove 12 or on the guide wire GW. Application of a liquid to the groove 12 may also be beneficial, in that the surface tension of the liquid may assist in guiding the guide wire GW into the selected catheter SC.

Figure 2:
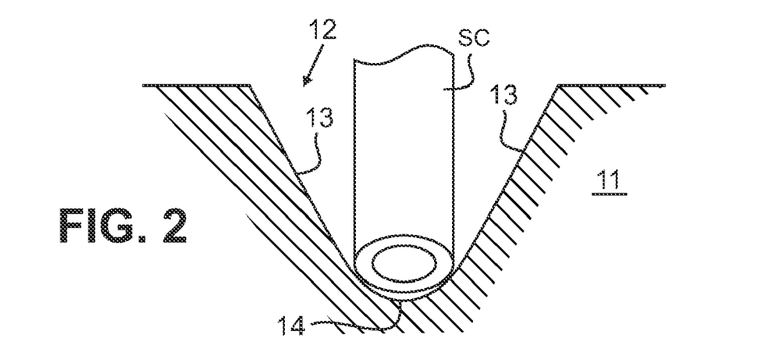
FIG. 2 is a sectional view of one type of cross-sectional contour that may be used in the invention of FIG. 1.

The groove 12 may have several different types of cross section and various depths. As shown in FIG. 1, the groove 12 may be substantially a semi-circular groove in the surface of the body 11. Alternatively, as shown in FIG. 2, the groove 12 may have sides 13 that taper inwardly toward a substantially concave cross-sectional contour 14 at the apex, or bottom, of the tapered groove 12. In FIG. 2, the concave contour is actually rounded, having a radius that substantially matches the outside radius of the catheter SC. It can also be seen that, while in FIG. 1, the groove 12 has a depth that is less than the outside diameter of the catheter SC, FIG. 2 shows that the groove 12 can alternatively have depth that is greater than the outside diameter of the catheter SC.

Figure 3:
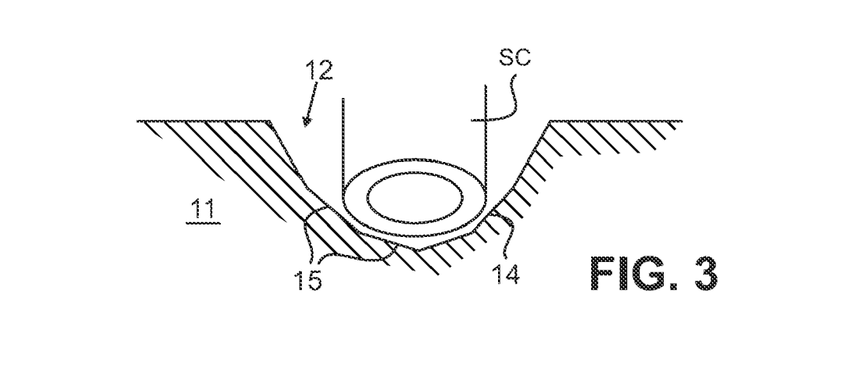
FIG. 3 is a sectional view of a second type of cross-sectional contour that may be used in the invention of FIG. 1.

FIG. 3 illustrates that, rather than having a rounded cross-sectional contour, the concave contour 14 at the bottom of the groove 12 can also be formed by a plurality of other surfaces, such as longitudinally arranged substantially flat surfaces 15 within the groove 12, with the flat surfaces forming a contour approximating a radiused curve. It is important that the spaces created by the joints between the flat surfaces, between the groove surface and the catheter, must be small enough to prevent entry of the end of the guide wire between the catheter and the groove surface. That is, the flat surfaces must be sufficiently narrow, and appropriately angled, to insure that the space between the flat groove surfaces and the catheter is less than the diameter of the guide wire. FIG. 3 also shows that this approximate radiused curve can also have a radius that substantially matches the outside radius of the catheter SC. Whether the concave contour 14 is round or formed from a plurality of flat surfaces, it is preferred that the concave contour 14 have a radius that is substantially the same as the outside radius of the catheter SC, plus or minus 10% of the catheter radius. Ideally, the concave contour 14 will have a radius that is no less than the outside radius of the catheter SC, and no greater than the outside radius of the catheter SC plus 10% of the catheter radius.

Figure 4:
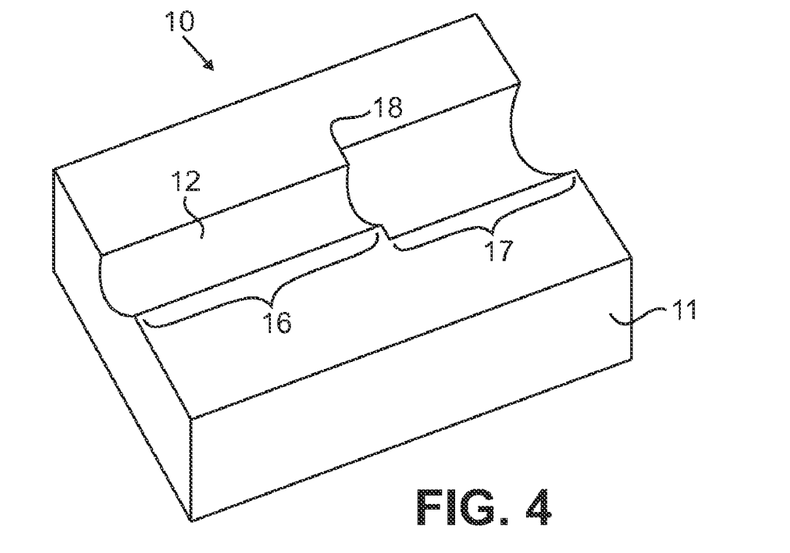
FIG. 4 is a perspective view of a second embodiment of a device according to the present invention.
Figure 5:
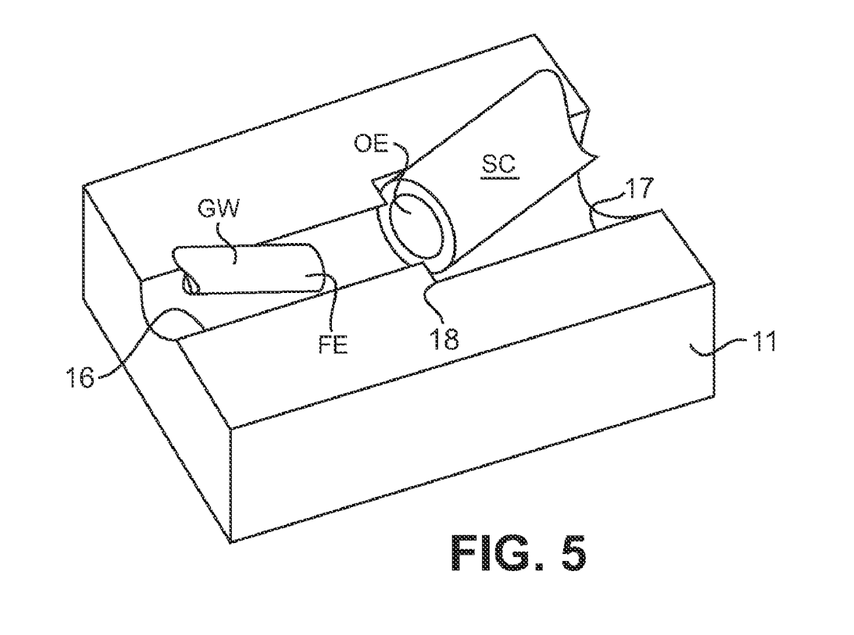
FIG. 5 is a perspective view of the embodiment of FIG. 4 in use with a guide wire and a catheter.

As shown in FIG. 4, the groove 12 can have two segments or portions 16, 17, with a first segment 16 having a shallower depth and/or a smaller radius than the second segment 17. This forms a discontinuity 18 at the point where the two groove portions 16, 17 meet, end-to-end. At the discontinuity 18, the depth and/or radius of the groove 12 change from the shallower depth and/or smaller radius of the first portion 16 to the deeper depth and/or larger radius of the second portion 17. It is also usually advantageous to have the center of radius, or axis, of the first portion 16 of groove 12 aligned with the center of radius, or axis, of the second portion 17 of the groove 12. FIG. 5 shows this embodiment of the invention 10 in use. First, the open end OE of the selected catheter SC is placed in the second portion 17 of the groove 12, and the open end OE of the selected catheter SC is slid along this deeper/larger radiused portion 17 of the groove 12, until the open end OE abuts the discontinuity 18. Then, the free end FE of the guide wire GW is placed in the first portion 16 of the groove 12, and the free end FE of the guide wire GW is slid along this shallower/smaller radiused portion 16 of the groove 12, until the free end FE of the guide wire GW enters the open end OE of the selected catheter SC. In some applications, having this disparity between the depths and/or radii of the two portions 16, 17 of the groove 12 makes it easier to thread a guide wire GW into a selected catheter SC, or some other tubular instrument.

Figure 6:
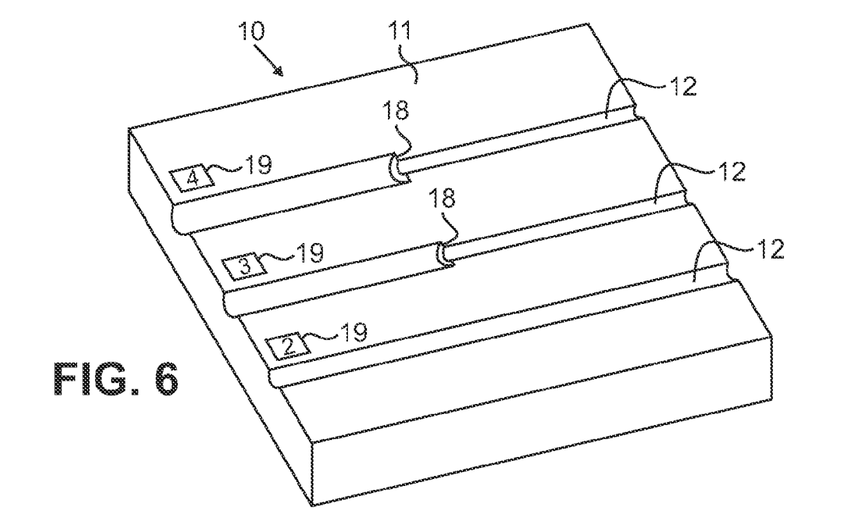
FIG. 6 is a perspective view of a third embodiment of a device according to the present invention.

FIG. 6 illustrates that the device 10 can have a plurality of open grooves 12 in the body 11. Each of the grooves 12 can be formed with a different depth and/or a different radius on its bottom contour. Some grooves 12 may have discontinuities 18, and others may be continuous. Each groove 12 should have a label 19 which can indicate the depth, bottom contour shape, or radius of the groove, as well as whether the groove 12 is continuous or has a discontinuity 18.

Figure 7:
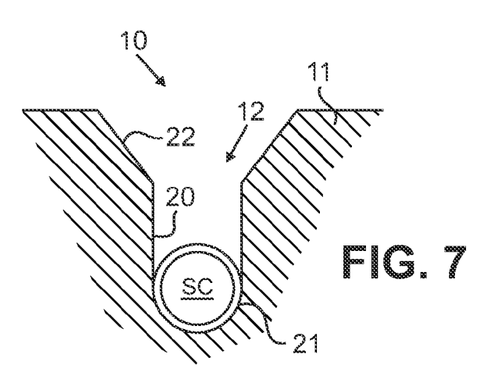
FIG. 7 is a cross-sectional view of a groove, illustrating a bottom profile consisting of vertical sides culminating in a rounded contour.

It has been found that the present invention functions in an optimum fashion if the shape of at least the catheter portion of the groove 12 has certain specific characteristics. While these characteristics are not critical to the invention, they add to its functionality. Specifically, as shown in FIG. 7, the groove 12 can have a bottom profile consisting of vertical sides 20 culminating in a rounded contour 21. The upper profile consists of sloped sides 22 that taper inwardly from the surface of the body 11 toward the upper ends of the vertical sides 20. The rounded contour 21 has a diameter that is the same as the outer diameter of the catheter SC. As a result, this rounded contour 21 makes full contact with a 180 degree radius of the periphery of the catheter SC, thereby gripping the catheter SC securely, but not impeding placement of the catheter SC into the groove 12. The vertical sides 20 extend upwardly from there. The full depth of the bottom profile of the groove 12, including the vertical sides 20 and the rounded contour 21, is approximately twice the diameter of the selected catheter SC. The sloped sides 22 assist in placing the catheter SC into the bottom profile 20, 21 of the groove 12.

Figure 8:
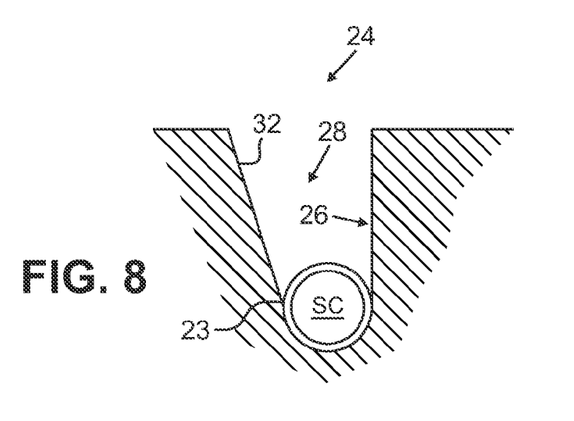
FIG. 8 is a cross-sectional view of another groove, illustrating a bottom profile consisting of one vertical side and one non-vertical side culminating in a rounded contour.

FIG. 8 illustrates another implementation in which the shape of the catheter and/or guide wire portion of the groove affords an optimum functionality. As with FIG. 7, implementing such shapes is not critical to the invention. As shown in FIG. 8, a groove 28 can have a bottom profile consisting of a substantially vertical wall 26 and a substantially non-vertical wall 32 culminating in a rounded contour 23. This profile may be considered an "eccentric" one due to the asymmetry of the walls. It should be noted that while the wall 26 is termed a "vertical" wall, it need not be exactly vertical—rather a small angle may be instituted in the wall, and the wall should still be considered substantially vertical. The substantially vertical wall and the substantially non-vertical wall may form an angle of between about 10 degrees and 50 degrees. While not shown in FIG. 8, but in the same way as in FIG. 7, the upper profile may further include sloped sides that taper inwardly from the surface of the body toward the upper end of the vertical side and the upper end of the non-vertical side. The rounded contour 23 may have a diameter that is substantially the same as the outer diameter of the catheter SC. As a result, this rounded contour 23 generally makes less than a 180-degree contact with the periphery of the catheter SC, thereby still gripping the catheter SC securely, but making placement of the catheter SC into the groove 28 even easier. For example, the angular segment over which contact is made may be between about 90 degrees and 180 degrees, and especially between about 90 degree and 120 degrees. In this way, the rounded contour makes substantial contact with the outer diameter of the catheter SC, while still allowing particularly convenient placement of the catheter SC into the groove 24.

As before, the full depth of the bottom profile of the groove 28, including the vertical and non-vertical sides 26 and 32 respectively, and the rounded contour 21, is approximately twice the diameter of the selected catheter SC.

Devices such as the kind described above are often located at, in, or near the surgical operating field. In fact, it is often highly convenient to locate them very close to the catheter insertion location. Accordingly, they may often be placed on the patient or adjacent the patient. During surgery, a patient is typically draped with multiple towels, leaving only the actual sterile field exposed. For this reason, it is desirable to be able to secure the device to one of these towels.

Figure 9A:
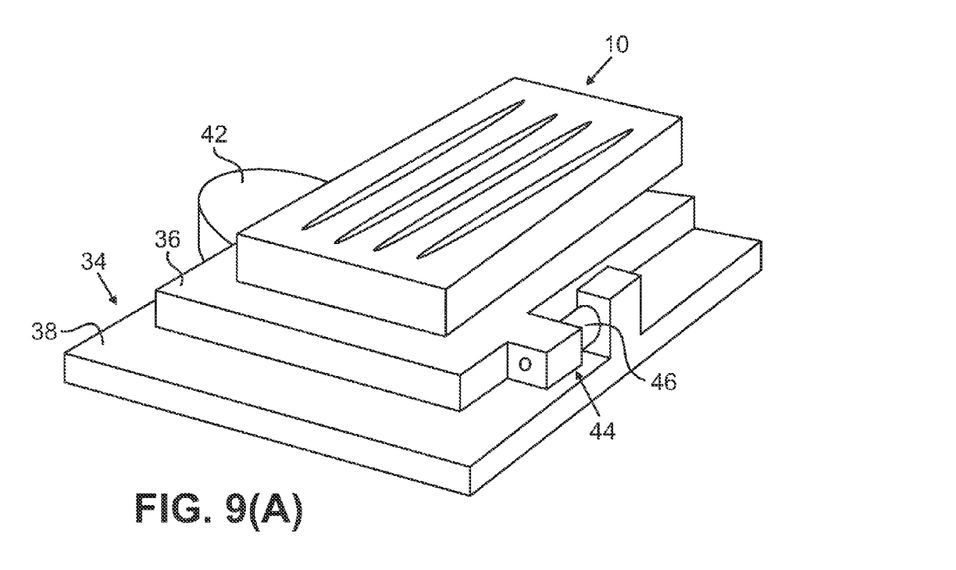
FIGS. 9(A) and 9(B) are perspective and side views, respectively, of a first embodiment of an attachment mechanism for attaching a device to a towel, e.g., as may be draping a patient during surgery, here implemented as a towel clamp with spring.
Figure 9B:
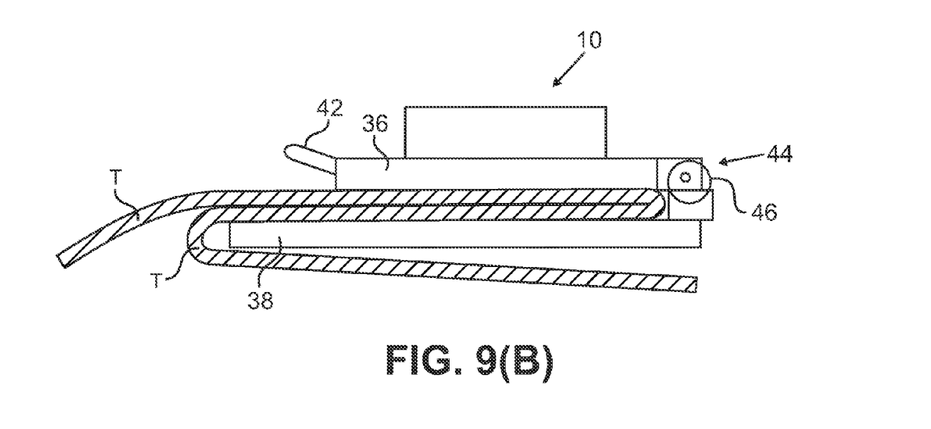

FIGS. 9(A) and 9(B) are perspective and side views, respectively, of a first embodiment of an attachment mechanism for attaching a device to a towel, e.g., as may be draping a patient during surgery, here implemented as a towel clamp with spring. In particular, a device 10 is illustrated that has a construction as described above. The device 10 is mounted to or formed integrally with an attachment mechanism, which in this case is a towel clamp with spring assembly 34. The towel clamp with spring assembly 34 includes an upper plate 36 and a lower plate 38 which are attached via a hinge assembly 44 which may include a spring 46. A pull tab 42 may extend from one extremity of the upper or lower plate (or both) for ease in attaching (and disengaging) the towel clamp from a towel T.

In use, a towel T is placed between the upper and lower plates. The spring forces the upper plate towards the lower one, frictionally securing the device 10 to the towel T. At any time, for installation or for removal, the pull tab 42 may be used to separate the upper from the lower plate.

Figure 10A:
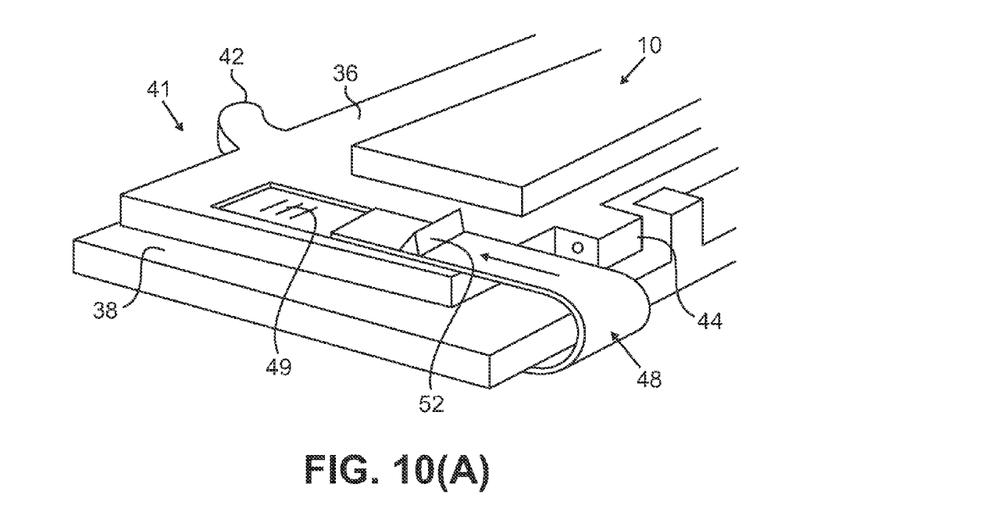
FIGS. 10(A) and 10(B) are perspective and side views, respectively, of a second embodiment of an attachment mechanism for attaching a device to a towel, e.g., here implemented as a towel clamp with clip.
Figure 10B:
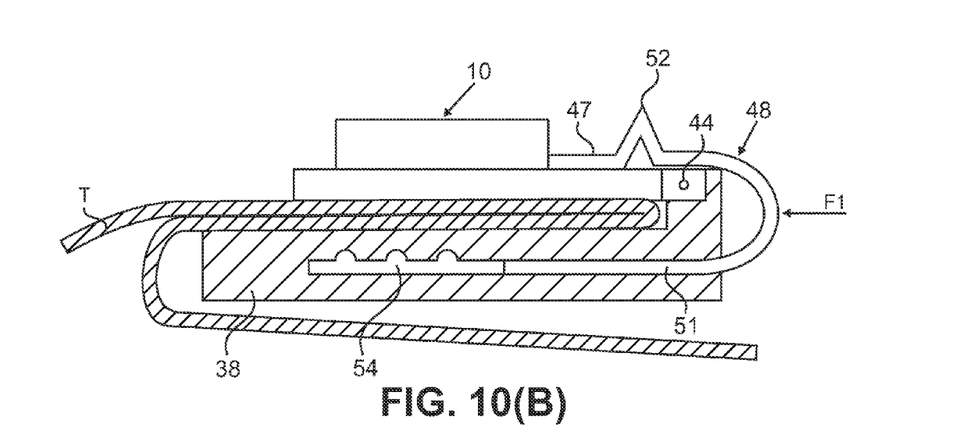

FIGS. 10(A) and 10(B) are perspective and side views, respectively, of a second embodiment of an attachment mechanism for attaching a device to a towel, e.g., here implemented as a towel clamp with clip. In particular, a device 10 of the above-described construction is mounted on or formed integrally with an attachment mechanism, shown in FIGS. 10(A) and 10(B) as a towel clamp with clip 41. Some elements are the same as in FIG. 9. For example, an upper plate 36 is coupled to a lower plate 38, and a pull tab 42 may extend from either (in FIGS. 10(A) and 10(B), from the upper plate). A hinge assembly 44 allows hinged movement of the plates. However, one of ordinary skill will recognize that the hinge assembly 44 is not necessary in all of these embodiments. For example, in FIGS. 10(A) and 10(B), the clip itself, as described below, may in some constructions be enough to hold the upper plate attached to the lower plate.

Referring again to FIGS. 10(A) and 10(B), a clip 48 is shown, which holds the upper plate to the lower plate. The clip 48 may ride in an optional track 49 for ease of placement. An internal slot 54 may also be employed such that the clip 48 has a lower arm 51 that enters the lower plate. The internal slot 54 is only shown in FIG. 10(B). It will be recognized that the track or internal slot may be employed on either the upper or lower plates, or both. However, in many implementations, it is easier to remove the clip if at least one plate does not employ an internal slot. For additional ease of installation and removal, a corrugation 52 may be disposed on an upper arm 47 of the clip 48.

For installation, a towel T is placed between the upper and the lower plates and the clip loaded into the track and/or internal slot (or just around the plates if neither a slot nor a track is employed). Force applied in the direction F1 secures the clip to the plates, and this secures the device 10 to the towel T.

Figure 11A:
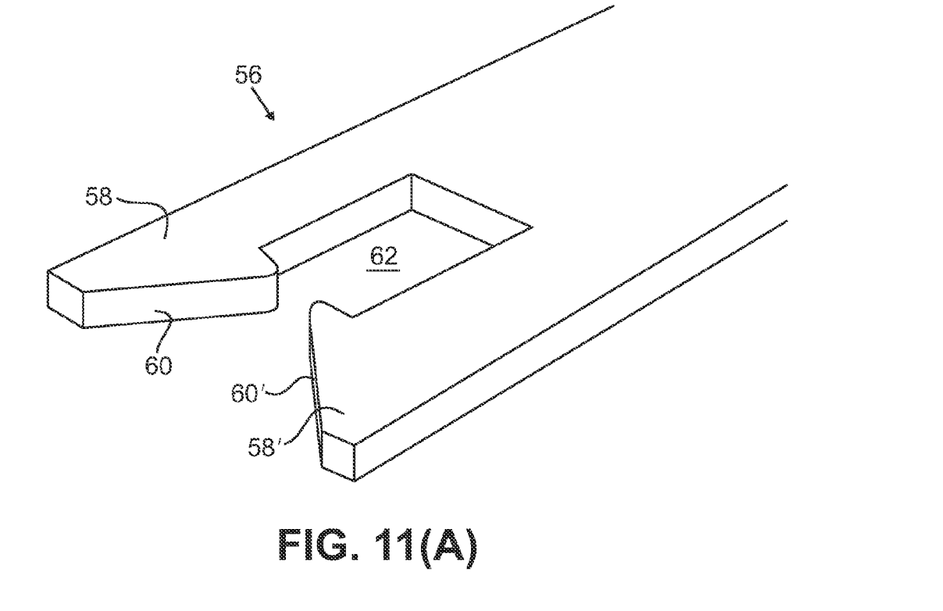
FIGS. 11(A) and 11(B) are perspective and side views, respectively, of a third embodiment of an attachment mechanism for attaching a device to a towel, e.g., here implemented as a flexible fork assembly, which may be employed with or without a spring.
Figure 11B:
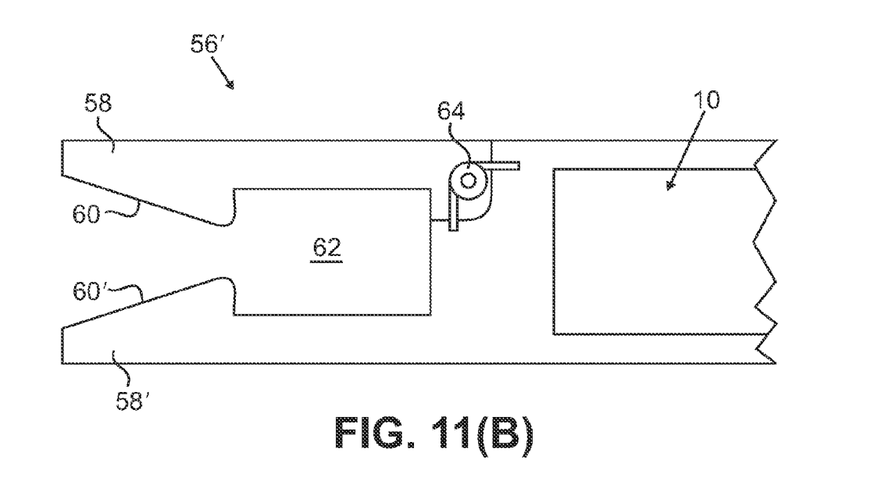

FIGS. 11(A) and 11(B) are perspective and side views, respectively, of a third embodiment of an attachment mechanism for attaching a device to a towel, e.g., here implemented as a flexible fork assembly. In particular, FIG. 11 shows a flexible fork assembly 56, which may be employed with (FIG. 11(A)) or without (FIG. 11(B)) a spring.

At least two tines 58 and 58' may form the fork 56. One or more tapered surfaces 60 and 60' may be employed to ease introduction of the towel portion into a hole 62 defined by the tines 58 and 58'.

In the implementation of FIG. 11(A), in use, the flexibility of the tines themselves may be configured to be enough to, upon installation of a towel portion, distend the tines and then bring the same back together to securely hold a towel.

In a related implementation, that of FIG. 11(B), a flexible fork assembly 56' is shown including a spring 64 attached to the tine 58. In a related implementation, a spring may be attached to the tine 58' as well. In these implementations, the flexibility of the fork tines is assisted by the angular resilience of the spring.

In use, a towel portion may be inserted into hole 62, and the same may be conveniently inserted through the use of tapered surfaces 60 and 60'. Generally, a sufficiently-large portion of the towel is inserted so that a sufficient friction-fit is achieved, such that the towel does not pull out of the hole. This requirement can also be employed to set the minimum spring constant (or stiffness) of the spring 64, in implementations where this element is used.

Figure 12A:
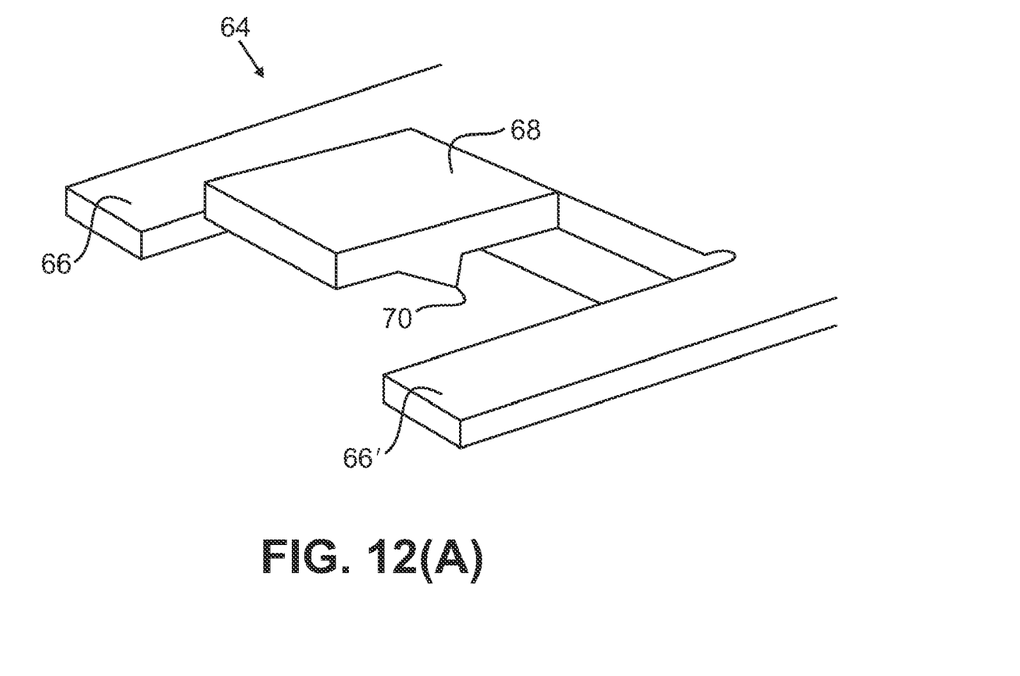
FIGS. 12(A) and 12(B) are perspective and side views, respectively, of a fourth embodiment of an attachment mechanism for attaching a device to a towel, e.g., here implemented as a flexible tab assembly.
Figure 12B:
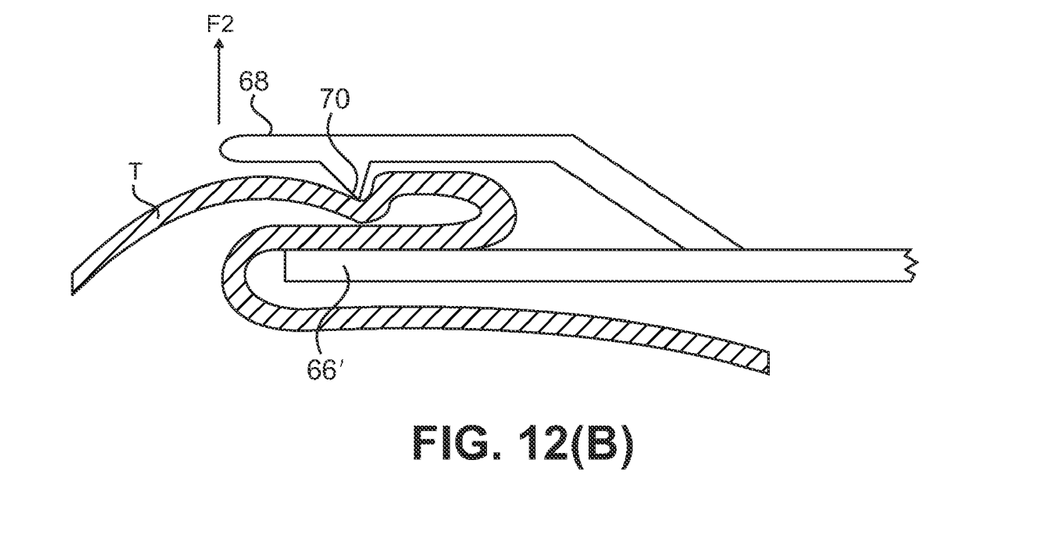

FIGS. 12(A) and 12(B) are perspective and side views, respectively, of a fourth embodiment of an attachment mechanism for attaching a guide-wire-loading device to a towel, e.g., here implemented as a flexible tab assembly 64. While the guide-wire-loading device is not shown in the figure, the same may be mounted on, coupled to, or formed integrally with the attachment mechanism. The flexible tab assembly 64 includes at least two tines 66 and 66' as well as a flexible tab 68. A burr 70 may be formed on the flexible tab 68 to allow an enhanced gripping effect on a towel portion T. As shown in FIG. 12(B), a towel portion T may be gathered and forced between the tines 66 and 66' and under the flexible tab 68. In this way, a towel may be secured in the flexible tab assembly 64, and thus the guide wire-loading device may be secured to a towel T. To release the towel, a force in the direction F2 may be exerted on the flexible tab 68.

Figure 13A:
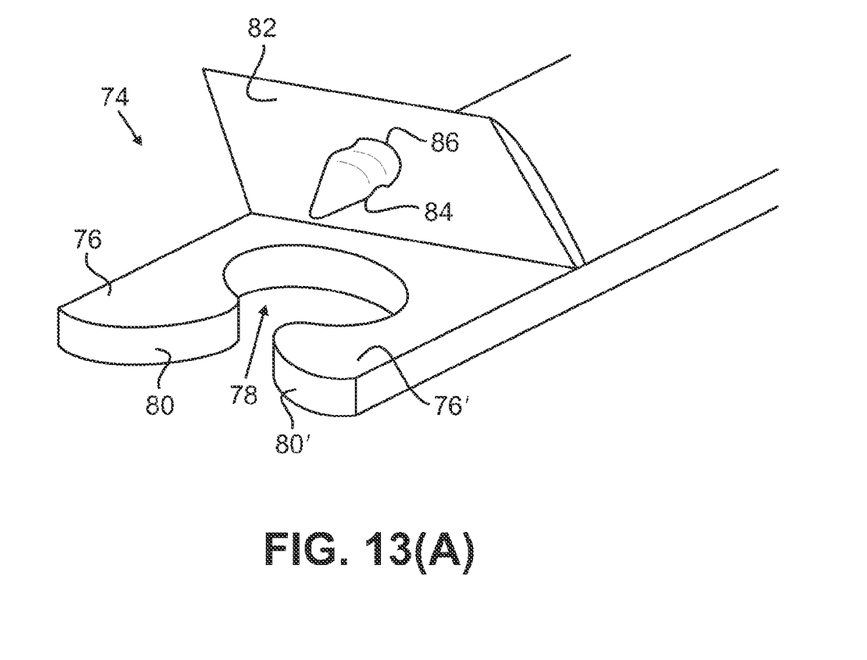
FIGS. 13(A) and 13(B) are perspective and side views, respectively, of a fifth embodiment of an attachment mechanism for attaching a device to a towel, e.g., here implemented as a hinged cover with a snap-button assembly.
Figure 13B:
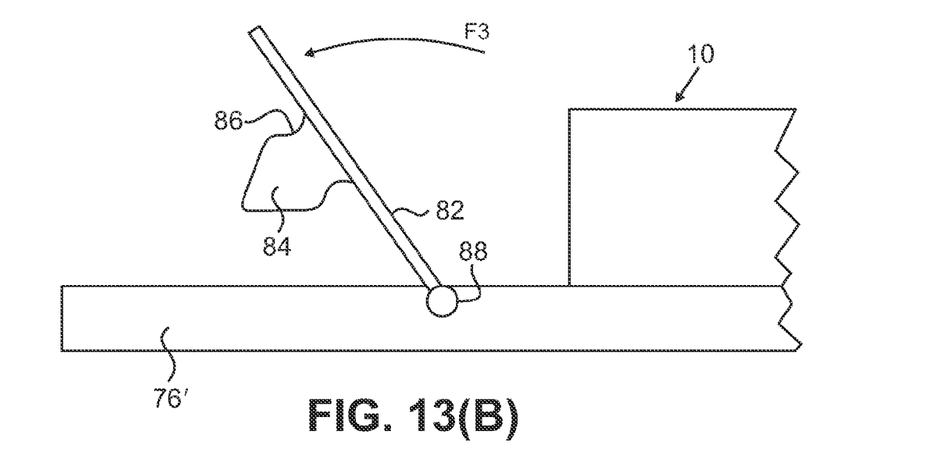

FIGS. 13(A) and 13(B) are perspective and side views, respectively, of a fifth embodiment of an attachment mechanism for attaching a guide wire-loading device to a towel, e.g., here implemented as a hinged cover with a snap-button assembly 74. In particular, two opposing segments 76 and 76' define a hole 78 into which a towel (not shown) may be drawn. The hole 78 is shown as substantially circular, but the shape is not critical. The segments 76 and 76' may include respective tapered surfaces 80 and 80' to ease introduction of a towel into the hole 78. A hinged cover 82 is shown, which is attached to the segments 76 and 76' by a hinge 88. A neck 86 extends from the cover 82, and a snap button 84 is attached to the neck 86.

When a towel portion has been pulled through the hole 78, the cover 82 may be closed in the direction indicated by arrow F3. This action secures the towel in the hole 78 and thus secures the guide wire-loading device to the towel. In one implementation, as shown, the snap button 84 has a bulbous shape; this shape assists in the securing of the snap button within the hole. However, other shapes may also be employed. For removal, the user may pull up on the cover 82 to pull the snap button 84 out of engagement with the hole 78.

Figure 14A:
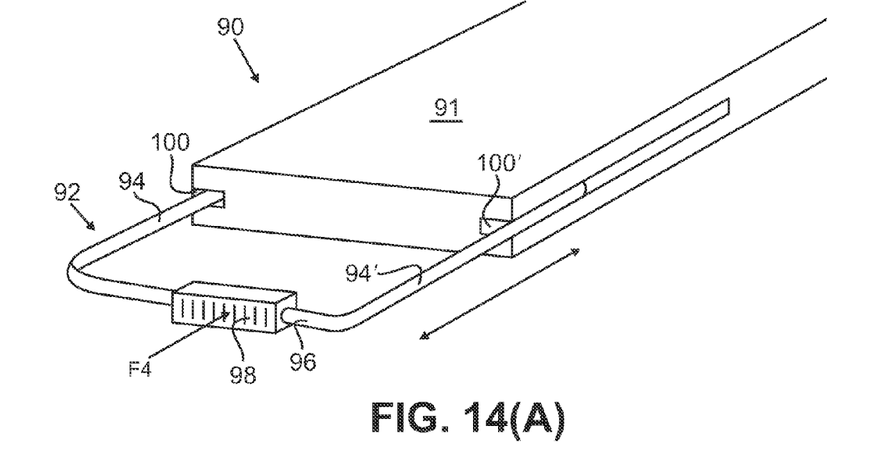
FIGS. 14(A) and 14(B) are perspective and side views, respectively, of a sixth embodiment of an attachment mechanism for attaching a device to a towel, e.g., here implemented as a sliding wire capture lock.
Figure 14B:
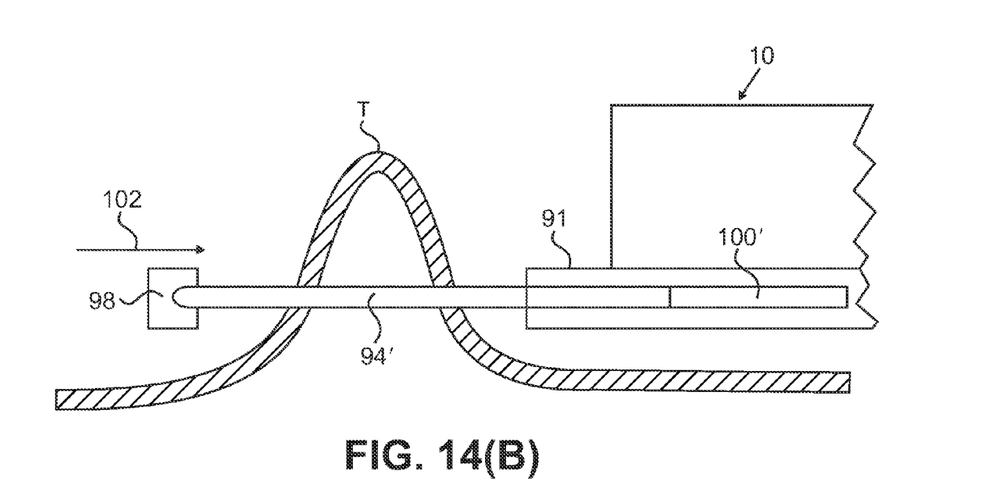

FIGS. 14(A) and 14(B) are perspective and side views, respectively, of a sixth embodiment of an attachment mechanism for attaching a device to a towel, e.g., here implemented as a sliding wire capture lock 90. As above, the same may be coupled to or formed integrally with a guide wire-loading device 10. The sliding wire capture lock 90 includes a housing 91 in which are formed two slots 100 and 100'. A sliding wire 92 includes two longitudinal segments 94 and 94' which slide in the respective slots 100 and 100'. A cross segment 96 connects segments 94 and 94'. A tab 98 may be formed on the cross segment 96, to allow ease of pushing during installation and ease of pulling during removal. Ribbing or other contouring may be employed on one or both sides of the tab 98 to enhance the ability of a user to grip the tab 98 as well as to enhance gripping of a towel portion T.

In use, a towel portion T is placed in the hole formed by segments 94, 94', 96, and the housing 91. The sliding wire 92 is then pushed toward the housing 91 in the direction indicated by arrow 102 (force F4). The towel T is thus captured, and the guide wire-loading device is thus secured to the towel T. For removal, the sliding wire 92 is pulled out in a direction opposite that of installation, and the towel T removed.

Figure 15A:
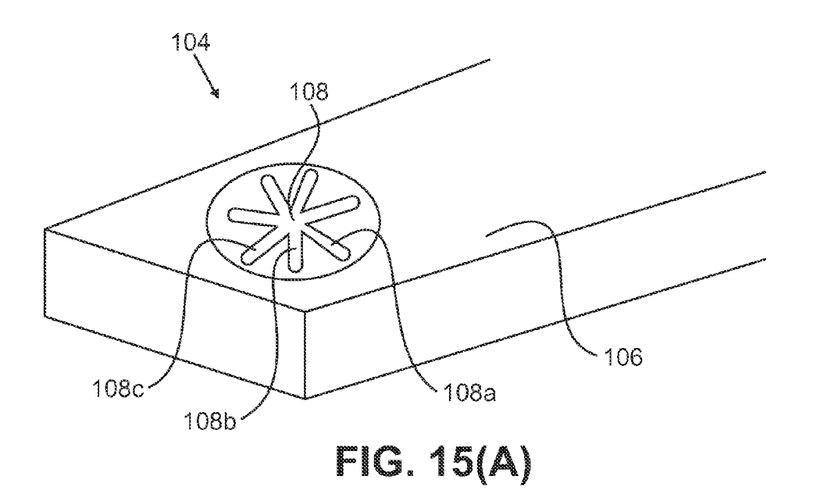
FIGS. 15(A) and 15(B) are perspective and side views, respectively, of a seventh embodiment of an attachment mechanism for attaching a device to a towel, e.g., here implemented as a gripping ring with flexible fingers.
Figure 15B:
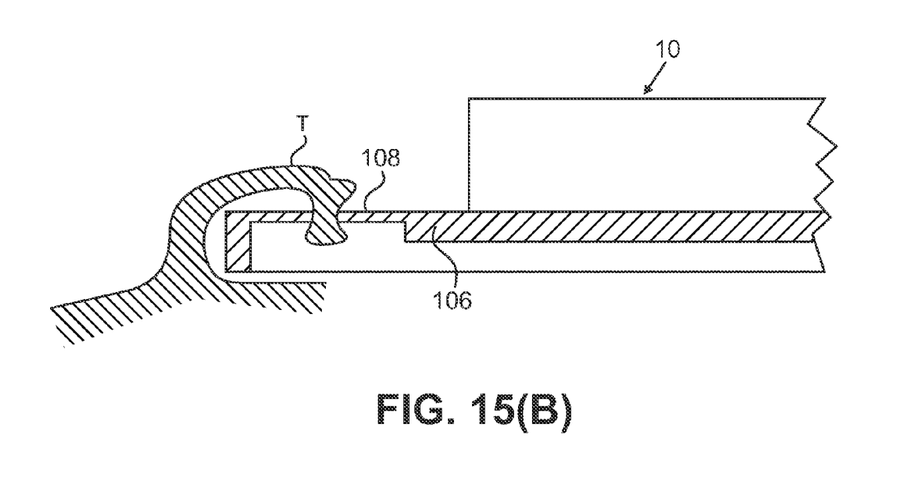

FIGS. 15(A) and 15(B) are perspective and side views, respectively, of a seventh embodiment of an attachment mechanism for attaching a guide wire-loading device to a towel, e.g., here implemented as a gripping ring assembly 104 with flexible fingers. This assembly 104 includes a housing 106 coupled to (or as above, integral with) the guide wire-loading device 10 (shown in FIG. 15(B)). A gripping ring 108 is formed in the housing, and the same includes a number of flexible fingers 108a, 108b, and so on. The gripping ring 108 and flexible fingers 108i may be formed of, e.g., various plastic or rubber materials in order to allow sufficient flexibility to receive a portion of a towel T, secure the same against removal during normal use, and allow the towel to be removed following use. In use, as shown in FIG. 15(B), a portion of a towel T may be inserted into the gripping ring. The stiffness of the fingers 108i prevents removal of the towel until the procedure is completed, at which time the towel may be removed.

Figure 16A:
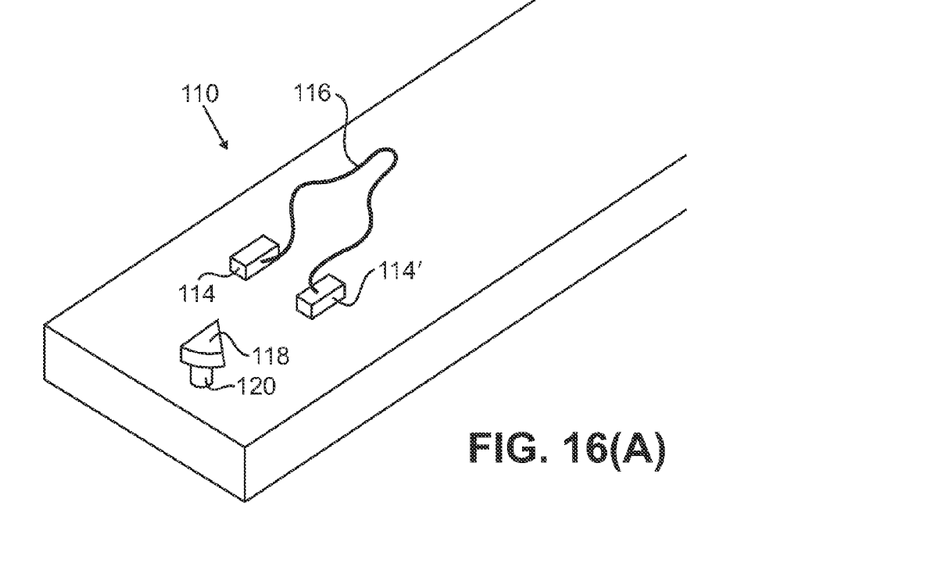
FIGS. 16(A) and 16(B) are perspective and side views, respectively, of a eighth embodiment of an attachment mechanism for attaching a device to a towel, e.g., here implemented as a capture wire with engagement button assembly.
Figure 16B:
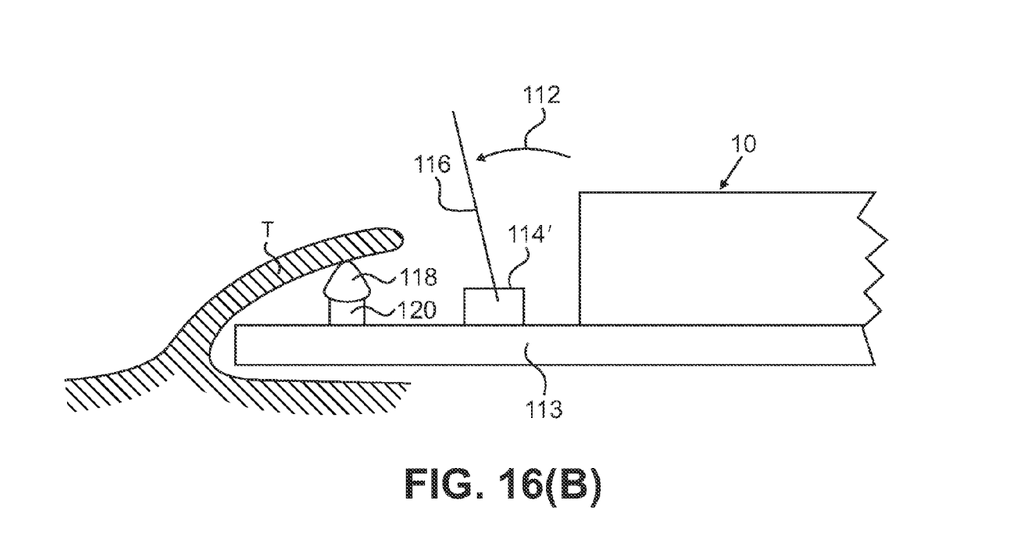

FIGS. 16(A) and 16(B) are perspective and side views, respectively, of an eighth embodiment of an attachment mechanism for attaching a guide wire-loading device to a towel, e.g., here implemented as a capture wire with engagement button assembly 110. The assembly 110 includes two supports 114 and 114' to which is mounted a capture wire 116. The supports 114 and 114' are mounted on a housing 113. Also mounted on the housing 113 is an engagement button 118 via a neck 120.

In use, a towel T is placed over the engagement button 118, and the capture wire 116 is then moved in an angular direction 112 and placed over the top of the towel T and the engagement button 118. The shape of the capture wire 116 and that of engagement button 118 may cooperate to secure the towel in position, or alternatively the securing may be accomplished only by way of friction fit with no particular shapes involved.

To remove, the capture wire 116 is pulled away from the top of the engagement button 118, and the towel removed.

Figure 17A:
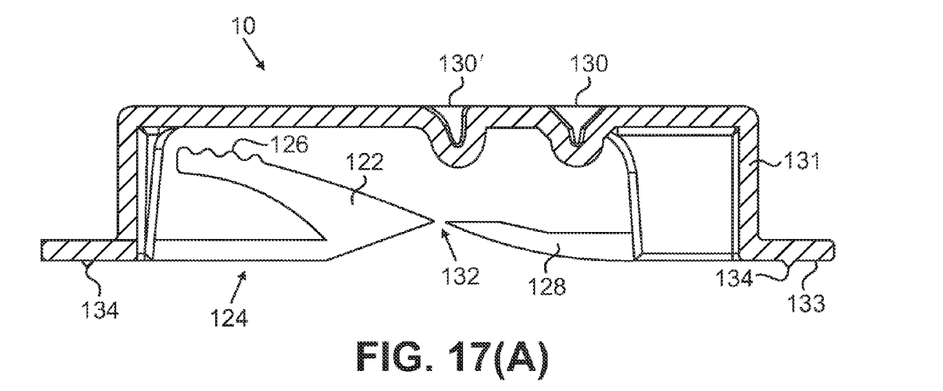
FIGS. 17(A) and 17(B) are side and perspective views, respectively, of a ninth embodiment of an attachment mechanism for attaching a device to a towel, e.g., here implemented as sets of opposing fingers. In these figures, as well, an implementation of the device is shown, having two grooves without abutments and six grooves with abutments and rounded ends, for threading guide wires through certain catheters having rounded ends.
Figure 17B:
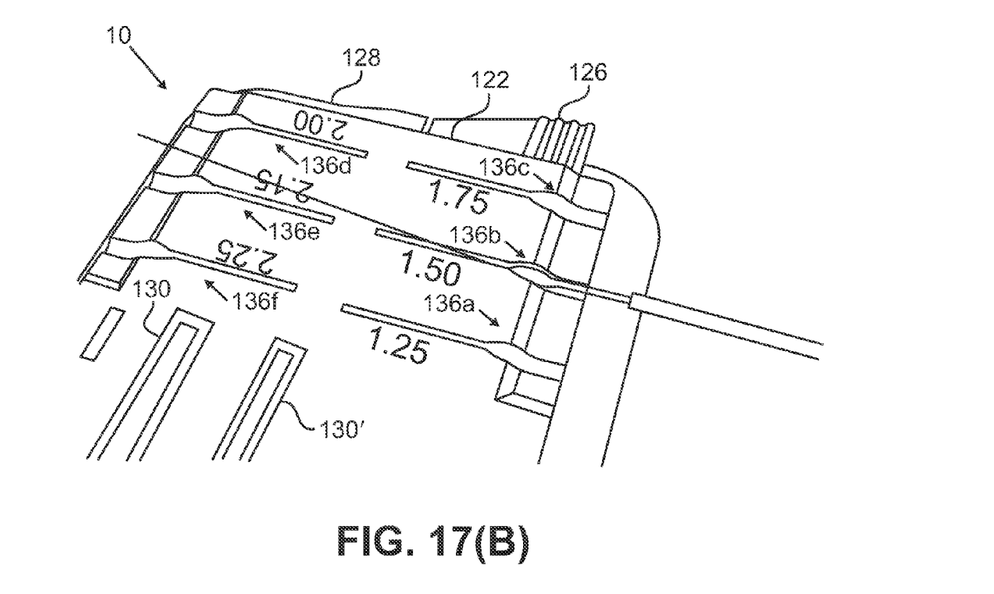

FIGS. 17(A) and 17(B) are side and perspective views, respectively, of a ninth embodiment of an attachment mechanism for attaching a guide wire-loading device 10 to a towel, e.g., here implemented as an assembly 124 of opposing fingers. In these figures, as well, an implementation of the device is shown, having two grooves without abutments and six grooves with abutments and rounded ends, the latter for threading guide wires through certain catheters having rounded ends.

The device 10 includes a housing 131, and defined within the housing 131 is a groove 130 and an eccentric groove 130'. The grooves 130 and 130' may be of the types described above. A flat portion 133 of the housing 131 may include protuberances 134 which help to grip the towel and further prevent movement of the device 10. The protuberances are generally formed on a bottom surface of the housing or body. Mounted to or integral with the device 10 is the assembly 124 of opposing fingers. In FIGS. 17(A) and 17(B), the assembly 124 includes a first finger 122 separated by a substantially opposing finger 128. Distal ends of the fingers 122 and 128 are separated by a gap 132. A portion of one or both fingers 122 and 128 may include ribs 126 for ease in gripping. In the structure of FIGS. 17(A) and 17(B), only one finger (finger 122) (per set) is shown with ribs 126.

FIG. 17(B) illustrates a perspective view of the attachment mechanism, as well as one implementation of the guide wire-loading device 10. As may be seen in both figures, a non-eccentric groove 130 is formed in the device, as well as an eccentric groove 130'. A series of variously-sized grooves 136a-136f are also formed, these including abutments and featuring bead-shaped catheter grooves to accommodate devices such as the Rotablator® noted above. As will be understood, any number of other configurations may be employed as well, depending on the situation. The use of the device is as described above.

In use, a towel may be drawn into the gap 132 and held in place by frictional engagement with fingers 122 and 128. To remove, the gap 132 is made larger to allow the towel to escape the frictional engagement. In the configuration of FIGS. 17(A) and 17(B), one way to increase the size of the gap 132 is to push on the ribs 126, thereby deflecting a distal tip of the finger 122. Other ways of increasing the size of this gap will also be understood, given this teaching.

Suitable materials for use in major components of the attachment mechanisms described above, as well as the device for guide wire loading, include blow- or injection-molded plastics, or the like. The guide wire-loading device may be single-use disposable or reusable.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

The invention claimed is:

1. A medical device for loading a medical guide wire into a selected tubular medical instrument having a selected outside radius, said medical loading device comprising:
   a body having a top surface and a bottom surface; and
   a plurality of open grooves formed in the top surface of said body for receiving medical guidewires and tubular medical instruments;
      wherein each of said plurality of open grooves further comprises:
         sides that extend within said body and from said top surface of said body; and
         a rounded contour at the bottom of said sides, said rounded contour having a cross section with a radius that matches said outside radius of said selected tubular medical instrument to within plus or minus 10%; and
      wherein said sides and said rounded contour of said plurality of open grooves have a combined depth greater than the outside diameter of said selected tubular instrument;
   wherein at least one but not all of said plurality of open grooves includes a first portion having a shallower depth than a second portion of said at least one of said plurality, said first portion of said groove having a first rounded contour with a smaller radius than a second rounded contour in said second portion of said groove; and
   wherein a different rounded contour is formed in each of at least two of said plurality of grooves, said different contours corresponding to the outside radii of a plurality of different sized selected tubular medical instruments; and
   an attachment mechanism coupled to the body, the attachment mechanism for securing the body to a fabric.

2. The medical device recited in claim 1, wherein the fabric is a towel for draping a patient.

3. The medical device recited in claim 1, wherein the attachment mechanism is selected from the group consisting of: towel clamps with springs or clips, flexible fork assemblies, flexible tabs, hinged tabs, wire capture systems, gripping rings with flexible fingers, wire-and-plug capture systems, and opposing finger towel capture systems.

4. The medical device recited in claim 3, wherein the attachment mechanism is an opposing finger towel capture system, and wherein an opposing finger towel capture system is disposed on at least two substantially opposite sides of the body.

5. The medical device recited in claim 1, further comprising protuberances disposed on the bottom surface of the body.

6. The medical device recited in claim 1, wherein at least two open grooves are formed in the top surface of said body, wherein each said open groove has a cross section shaped to substantially match said outside radius of said selected tubular medical instrument.

7. A method for loading a medical guide wire into a selected tubular medical instrument, said method comprising:
   providing a medical device, the medical device comprising:
      a body having a top surface and a bottom surface; and
      a plurality of open grooves formed in the top surface of said body for receiving medical guidewires and tubular medical instruments;
         wherein each of said plurality of open grooves further comprises:
            sides that extend within said body and from said top surface of said body; and
            a rounded contour at the bottom of said sides, said rounded contour having a cross section with a radius that matches said outside radius of said selected tubular medical instrument to within plus or minus 10%; and
      wherein said sides and said rounded contour of said plurality of open grooves have a combined depth greater than the outside diameter of said selected tubular instrument;
      wherein at least one but not all of said plurality of open grooves includes a first portion having a shallower depth than a second portion of said at least one of said plurality of open grooves, said first portion of said groove having a first rounded contour with a smaller radius than a second rounded contour in said second portion of said groove; and wherein a different rounded contour is formed in each of at least two of said plurality of grooves, said different contours corresponding to the outside radii of a plurality of different sized selected tubular medical instruments; and an attachment mechanism coupled to the body, the attachment mechanism for securing the body to a fabric;

attaching the medical device to a towel draping a patient using an attachment mechanism;

placing an open end of said tubular medical instrument in said groove at an angle;

placing an end of said medical guide wire in said groove at an angle; and moving said medical guide wire and said tubular medical instrument toward each other until said medical guide wire enters said open end of said tubular medical instrument.

8. The method recited in claim 7, wherein the step of attaching the medical device to a towel includes inserting the towel between two opposing fingers.

9. A medical device for loading a medical guide wire into a selected tubular medical instrument having a selected outside radius, said medical loading device comprising:

a body having a flat surface; and a plurality of open grooves formed in the flat surface of said body;

wherein each of said plurality of open grooves further comprises:

sides that extend within said body and from said flat surface of said body; and a rounded contour at the bottom of said sides, said rounded contour having a cross section with a radius that matches said outside radius of said selected tubular instrument to within plus or minus 10%; and wherein said sides and said rounded contour of said open groove have a combined depth greater than the outside diameter of said selected tubular medical instrument;

wherein at least two of said plurality of open grooves includes first portions having shallower depths than second portions, said first portion of said groove having a first rounded contour with a smaller radius than a second rounded contour in said second portion of said groove, and wherein said at least two of said plurality of open grooves include a commonly-sized first rounded contour;

wherein a different rounded contour is formed in each of at least two of said plurality of grooves, said different contours corresponding to the outside radii of a plurality of different sized selected tubular medical instruments; and an attachment mechanism coupled to the body, the attachment mechanism for securing the body to a fabric.

* * * * *